US012714877B2

(12) United States Patent
Parsons

(10) Patent No.: US 12,714,877 B2
(45) Date of Patent: Aug. 25, 2026

(54) LIGHT EMITTING FACE MASKS

(71) Applicant: SharkNinja Operating LLC, Needham, MA (US)

(72) Inventor: Olivia Louise Parsons, Boston, MA (US)

(73) Assignee: SharkNinja Operating LLC, Needham, MA (US)

( * ) Notice: Subject to any disclaimer, the term of this patent is extended or adjusted under 35 U.S.C. 154(b) by 223 days.

(21) Appl. No.: 18/411,806

(22) Filed: Jan. 12, 2024

(65) Prior Publication Data

US 2025/0229101 A1 Jul. 17, 2025

(51) Int. Cl.
*A61N 5/06* (2006.01)
*A61N 5/00* (2006.01)

(52) U.S. Cl.
CPC ...... *A61N 5/0616* (2013.01); *A61N 2005/007* (2013.01); *A61N 2005/0648* (2013.01); *A61N 2005/0652* (2013.01)

(58) Field of Classification Search
CPC .......... A61N 2005/0652; A61N 5/0616; A61N 2005/0647; A61N 2005/0659; A61N 2005/0663; A61N 2005/0645; A61N 2005/0666; A61N 2005/0626; A61N 2005/0654; A61N 2005/0628; A61N 5/067; A61N 2005/0627; A61N 2005/0648; A61N 2005/0665; A61N 2005/0662; A61N 5/062; A61N 5/0617; A61N 2005/0644; A61N 1/0472; A61N 2005/005; A61N 2005/007; A61N 5/0618; A61N 1/0408;

(Continued)

(56) References Cited

U.S. PATENT DOCUMENTS 7,748,387 B1 7/2010 Vu et al.
9,789,333 B2 10/2017 Tapper et al.
(Continued)

FOREIGN PATENT DOCUMENTS

CN 103861214 B 4/2016
CN 106955426 A 7/2017
(Continued)

OTHER PUBLICATIONS

Lee Chan Bong, Multifunction LED Mask With Eye Massage Function, Apr. 4, 2022 (Year: 2022).*

(Continued)

*Primary Examiner* — Jon Eric C Morales
(74) *Attorney, Agent, or Firm* — Mintz, Levin, Cohn, Ferris, Glovsky and Popeo, P.C. US

(57) ABSTRACT

Various illustrative systems, devices, and methods for face masks are provided. In general, a face mask is configured to provide light therapy to a user wearing the face mask. In an exemplary implementation, the face mask includes a light assembly configured to apply light therapy to a user wearing the face mask. The light assembly includes a plurality of lights, such as light emitting diodes (LEDs), configured to emit light and thereby provide light therapy to the user's face. The face mask also includes a protective member configured to protect the user's eyes from the light emitted by the lights. The protective member is configured to form a seal against the face of the user wearing the face mask and is configured to dynamically conform to a user's face.

15 Claims, 9 Drawing Sheets

(58) Field of Classification Search

CPC .................... A61N 1/0492; A61N 1/06; A61N 2005/0606; A61N 2005/0629; A61N 2005/0642; A61N 2005/0653; A61N 5/06; A61N 5/0621; A61N 1/0452; A61N 1/0456; A61N 2/002; A61N 2005/063; A61N 2005/0661; A61N 5/0601; A61N 5/0613; A61N 5/0619; A61N 5/0624; A61N 1/0476; A61N 1/048; A61N 1/0488; A61N 1/321; A61N 1/328; A61N 1/36014; A61N 1/36021; A61N 1/36046; A61N 2/02; A61N 2005/0651; A61N 2005/0664; A61N 2007/0034; A61N 7/00; A61N 1/20; A61N 1/22; A61N 1/30; A61N 1/36; A61N 2/00; A61N 2/06; A61N 2005/0607; A61N 2005/0632; A61N 2005/0643; A61N 2005/065; A61N 2005/0656; A61N 2005/073; A61N 5/0603; A61N 5/0622; A61B 2017/00057; A61B 2018/00642; A61B 2018/00791; A61B 2018/00988; A61B 2090/049; A61B 18/203; A61B 2018/00452; A61B 2090/0803; A61B 2018/00476; A61B 2090/036; A61B 2017/00084; A61B 2018/00005; A61B 2090/065; A61B 2018/00041; A61B 2018/00458; A61B 2018/0047; A61B 2018/2261; A61B 18/20; A61B 18/22; A61B 2017/00026; A61B 2017/00061; A61B 2017/00066; A61B 2017/00106; A61B 2017/00172; A61B 2017/00734; A61B 2017/00747; A61B 2017/00752; A61B 2017/00756; A61B 2017/00769; A61B 2018/00011; A61B 2018/00023; A61B 2018/00702; A61B 2018/00708; A61B 2018/00785; A61B 2018/00827; A61B 2018/00904; A61B 2018/1807; A61B 5/0059; A61B 5/01; A61B 5/0531; A61B 5/411; A61B 5/445

See application file for complete search history.

(56) References Cited

U.S. PATENT DOCUMENTS

| | | | |
|---|---|---|---|
| 9,814,905 | B2 | 11/2017 | Tapper et al. |
| 10,022,555 | B2 | 7/2018 | Tapper et al. |
| 10,610,001 | B2 | 4/2020 | Kim |
| 10,765,885 | B2 | 9/2020 | Schanze |
| D903,887 | S | 12/2020 | Althoff et al. |
| 11,020,607 | B2 | 6/2021 | Song |
| 11,077,319 | B2 | 8/2021 | Tapper et al. |
| 11,123,572 | B2 | 9/2021 | Dijkstra et al. |
| 11,517,639 | B2 | 12/2022 | Mldirim et al. |
| 11,642,546 | B2 | 5/2023 | Dai |
| 11,666,485 | B2 | 6/2023 | Luo |
| 11,815,692 | B1 | 11/2023 | Pickett et al. |
| 2015/0134033 | A1* | 5/2015 | Tapper ................ A61N 5/0616 607/90 |
| 2019/0336215 | A1 | 11/2019 | Mescher et al. |
| 2022/0080221 | A1 | 3/2022 | Gross |
| 2022/0152417 | A1 | 5/2022 | Kim |
| 2022/0212028 | A1 | 7/2022 | Lee |
| 2022/0219010 | A1 | 7/2022 | Kim |
| 2023/0013810 | A1 | 1/2023 | Luo |
| 2023/0165752 | A1 | 6/2023 | Woo |

FOREIGN PATENT DOCUMENTS

| | | | |
|---|---|---|---|
| CN | 107149725 | A | 9/2017 |
| CN | 107469237 | A | 12/2017 |
| CN | 106334268 | B | 8/2018 |
| CN | 109045482 | A | 12/2018 |
| CN | 107320853 | B | 3/2019 |
| CN | 106377846 | B | 6/2019 |
| CN | 110917507 | A | 3/2020 |
| CN | 111013023 | A | 4/2020 |
| CN | 111790058 | A | 10/2020 |
| CN | 112494806 | A | 3/2021 |
| CN | 111603678 | B | 10/2021 |
| CN | 113995964 | B | 3/2022 |
| CN | 114377299 | A | 4/2022 |
| CN | 111921082 | B | 7/2022 |
| CN | 115253086 | A | 11/2022 |
| CN | 115957446 | A | 4/2023 |
| CN | 110841208 | B | 5/2023 |
| CN | 116236702 | A | 6/2023 |
| CN | 113952108 | B | 7/2023 |
| CN | 116392724 | A | 7/2023 |
| CN | 114028728 | B | 8/2023 |
| CN | 115040788 | B | 8/2023 |
| CN | 116328196 | B | 10/2023 |
| EP | 3079566 | B1 | 4/2020 |
| EP | 3313507 | B1 | 4/2020 |
| EP | 3313508 | B1 | 4/2020 |
| KR | 20180035629 | A | 4/2018 |
| KR | 20210010130 | A | 1/2021 |
| KR | 102228378 | B1 | 3/2021 |
| KR | 20220042012 | A | 4/2022 |
| WO | 2020190059 | A1 | 9/2020 |
| WO | 2022045850 | A1 | 3/2022 |
| WO | 2022248793 | A1 | 12/2022 |
| WO | 2023031619 | A1 | 3/2023 |

OTHER PUBLICATIONS

International Search Report and Written Opinion received for PCT Application No. PCT/US2024/059542, mailed on Mar. 11, 2025, 20 pages.

U.S. Appl. No. 18/411,644 entitled "Face Masks With Noise Attenuation", filed on Jan. 12, 2024, 32 pages.

Invitation to Pay Additional Fees received for PCT Application No. PCT/US2024/059542 mailed on Jan. 30, 2025, 11 pages.

* cited by examiner

LIGHT EMITTING FACE MASKS

FIELD

The present disclosure generally relates to light emitting face masks.

BACKGROUND

Light can be used to treat various skin conditions, particularly the skin on a user's face. Therefore, face masks with one or more light sources may be used to emit light towards the user's face. However, the light is generally very bright and is typically directed at the user's entire face. Such direct exposure to light can cause eye problems, such as eyesight problems so the user has to close their eyes in order to avoid point-blank exposure to light.

Additionally, face masks are typically made of rigid materials in order to provide a stiff mounting surface for the light sources. However, rigid face masks can cause bruising, skin irritation, and pinching of the user's skin. These problems are exacerbated by repeated usage of the face mask, as is typical for face masks used to treat various skin conditions.

Accordingly, there remains a need for improved face masks.

SUMMARY

In general, systems, devices, and methods for face masks are provided.

In one aspect, an face covering device is provided that in one implementation includes a base, a plurality of light emitting diodes (LEDs), and a support assembly. The base is configured to cover at least a portion of a user's face and has formed therein a first eye opening and a second eye opening. The plurality of LEDs are coupled to the base and are configured to emit light toward and to skin of the user's face with the base covering at least the portion of the user's face. The support assembly is coupled to the base and includes a first eye support and a second eye support. The first eye support includes a first eyebrow support and a first portion of a nose support that together define a first eye support opening. The first eye support is configured to prevent the light emitted toward the user's face from passing through the first eye support opening. The second eye support includes a second eyebrow support and a second portion of the nose support that together define a second eye support opening. The second eye support is configured to prevent the light emitted toward the user's face from passing through the second eye support opening.

The face covering device can vary in any number of ways. For example, wherein the support assembly can have a shape that follows a shape of eyebrows, an inner side of a left eye, an inner side of a right eye, and a nose.

For another example, the face covering device can also include a first undereye support located under the first eye opening, the face covering device can also include a second undereye support located under the second eye opening, the first undereye support can further define the first eye support opening, and the second undereye support can further define the second eye support opening. Further, the first undereye support can be separate and distinct from the first eye support, and the second undereye support can be separate and distinct from the second eye support.

For yet another example, the support assembly can be configured to form a seal against the user's face.

For still another example, the support assembly can be configured to dynamically conform to the user's face.

For another example, the support assembly can include a compressible material coated by a protective coating. Further, the compressible material can include foam, and the protective coating can include silicone; and/or the base can be made from a rigid material.

For yet another example, the support assembly can be configured to facilitate supporting of the base over at least the portion of the user's face.

For another example, a number of the plurality of LEDs can be in a range between sixty diodes and one hundred diodes.

For still another example, the base can be configured to cover at least one of a user's chin, cheeks, and forehead. Further, the base can be configured to cover all of the user's chin, cheeks, and forehead.

For yet another example, the face covering device includes a support configured to be worn on a head of the user with the base covering at least the portion of the user's face. Further, the support can include a strap assembly.

For yet another example, the base can be made from a rigid material.

For another example, the base can have formed therein at least one of a mouth opening and a nose opening.

For still another example, the light emitted to the skin of the user face is configured to provide light therapy thereto.

In another implementation, a face covering device includes a base, a plurality of LEDs, and a support assembly. The base is configured to cover at least a portion of a user's face and has a first eye opening and a second eye opening. The plurality of LEDs are coupled to the base and are configured to emit light toward and to skin of the user's face with the base covering at least the portion of the user's face. The support assembly is coupled to the base and includes a nose support configured to contact at least a portion of the user's nose with the base covering at least the portion of the user's face, a first eyebrow support configured to contact at least one of an orbital bone of the user and a first one of a user's eyebrows with the base covering at least the portion of the user's face, and a second eyebrow support configured to contact at least one of the orbital bone of the user and a second one of a user's eyebrows with the base covering at least the portion of the user's face. A height of one or more of the nose support and the first and second eyebrow supports is configured to position the plurality of LEDs at a distance from the user's face with the base covering at least the portion of the user's face.

The face covering device can vary in any number of ways. For example, the distance can be in a range between about 10 mm and about 40 mm.

For another example, the distance of each LED of the plurality of LEDs from the user's face can be substantially equal for each LED.

For yet another example, the distance of at least one LED of the plurality of LED from the user's face can be different from the distance of at least one other of the plurality of LEDs.

For still another example, the height can be in a range between about 10 mm and about 40 mm.

For another example, the support assembly can include a foam coated by silicone.

For yet another example, the support assembly can be configured to form a seal against the user's face.

For still another example, the support assembly can be configured to dynamically conform to the user's face.

For another example, the support assembly can include a compressible material coated by a protective coating. Further, the compressible material can include foam, and the protective coating can include silicone; and/or the base can be made from a rigid material.

For yet another example, the support assembly can be configured to facilitate supporting of the base over at least the portion of the user's face.

For another example, the face covering device can also include a first undereye support located under the first eye opening, and a second undereye support located under the second eye opening.

For yet another example, a number of the plurality of LEDs can be in a range between sixty diodes and one hundred diodes.

For still another example, the base can be configured to cover at least one of a user's chin, cheeks, and forehead. Further, the base can be configured to cover all of the user's chin, cheeks, and forehead.

For yet another example, the face covering device includes a support configured to be worn on a head of the user with the base covering at least the portion of the user's face. Further, the support can include a strap assembly.

For another example, the base can have formed therein at least one of a mouth opening and a nose opening.

For yet another example, the base can be made from a rigid material.

For still another example, the light emitted to the skin of the user face is configured to provide light therapy thereto.

In another implementation, a face covering device includes a rigid base, a light assembly, and padding. The rigid base has a forehead portion configured to be worn at least partially over a user's forehead, a nose portion configured to be worn at least partially over the user's nose and cheeks, and a chin portion configured to be worn at least partially over the user's chin. The light assembly is coupled to the rigid base and is configured to emit light toward and to skin of the user's face. The padding is coupled to the base, is configured to prevent the light emitted toward the user's face from entering the user's eyes, and is configured to form a seal against the user's face.

The face covering device can vary in any number of ways. For example, the padding can include a nose support comprising a nose bridge support configured to contact a nose bridge of the user, a first nostril support configured to contact the nose of the user, and a second nostril support configured to contact the nose of the user; a first eyebrow support extending from a first side of the nose support; and a second eyebrow support extending from a second side of the nose support; the first eyebrow support can have one or more curves; and the second eyebrow support can have one or more curves.

For another example, the padding can be configured to prevent the light emitted toward the user's face from passing through first and second eye openings formed through the rigid base.

For yet another example, the first nostril support can extend laterally in a first direction from the first side of the nose support, the second nostril support can extend laterally from the second side of the nose support, and the first direction can be opposite the second direction.

For another example, the padding can include foam. Further, the foam can be coated with silicone.

For yet another example, each of the first and second nostril supports can have a height in a range between about 35 mm and about 40 mm, and/or each of the first and second eyebrow supports can have a length in a range between about 10 mm and about 20 mm.

For another example, the light assembly can include a plurality of LEDs. Further, a number of the plurality of LEDs can be in a range between sixty diodes and one hundred diodes.

For yet another example, the face covering device includes a support configured to be worn on a head of the user with the base covering at least the portion of the user's face. Further, the support can include a strap assembly.

For still another example, the light emitted to the skin of the user face is configured to provide light therapy thereto.

In another aspect, a method is provided that in one implementation includes powering a plurality of light emitting diodes (LEDs) of a face covering device worn on a face of a user such that the LEDs emit light toward and to skin of the user's face. The face covering device is worn on the face of the user with the face covering device forming a seal against the skin of the user's face such that the emitted is prevented from entering the user's eyes.

The method can vary in any number of ways. For example, the face covering device can include any one or more features of the face covering devices described above.

DESCRIPTION OF DRAWINGS

This disclosure will be more fully understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting embodiments and that the scope of the present invention is defined solely by the claims. The features illustrated or described in connection with one exemplary embodiment may be combined with the features of other embodiments. Such modifications and variations are intended to be included within the scope of the present invention.

Various illustrative systems, devices, and methods for face masks are provided. In general, a face mask is configured to provide light therapy to a user wearing the face mask. In an exemplary implementation, the face mask includes a light assembly configured to apply light therapy to a user wearing the face mask. The light assembly includes a plurality of lights, such as light emitting diodes (LEDs), configured to emit light and thereby provide light therapy to the user's face. The face mask also includes a support assembly configured to help support the face mask on the user's face. The support assembly is also configured to protect the user's eyes from the light emitted by the lights. The support assembly is configured to prevent light emitted from the lights from entering the user's eyes, thereby protecting the user's eyes from light damage and/or irritating the user with bright light during the delivery of the light therapy. The support assembly is configured to form a seal against the face of the user wearing the face mask to facilitate the blocking of the light from the user's eyes. The support assembly is configured to dynamically conform to a user's face, thereby allowing the support assembly to provide the seal regardless of the particular size and shape of the face of the user wearing the face mask. Therapy may thus be provided by the face mask while the face mask is comfortably positioned on the user's face and the user avoids direct exposure of light into their eyes.

In some implementations, a face covering device (also referred to herein as a "face mask" or "mask") is configured to provide light therapy and cooling therapy to a user wearing the face covering device. In other implementations, a face covering device is configured to provide light therapy without being configured to provide cooling therapy.

Figure 1A:
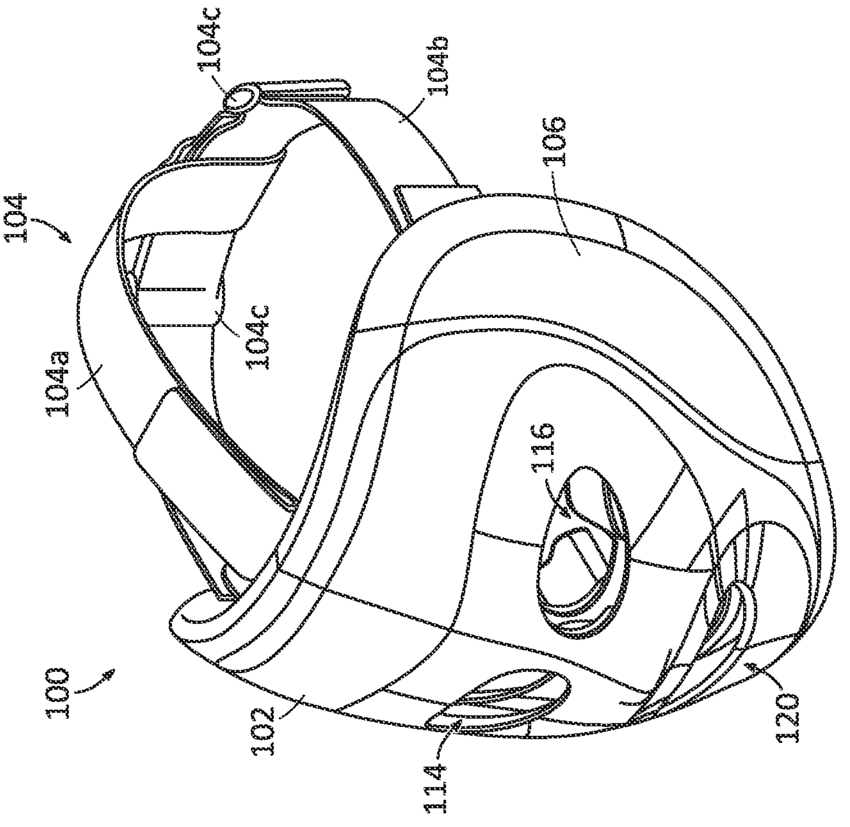
FIG. 1A is a perspective view of one implementation of a face covering device.
Figure 1B:
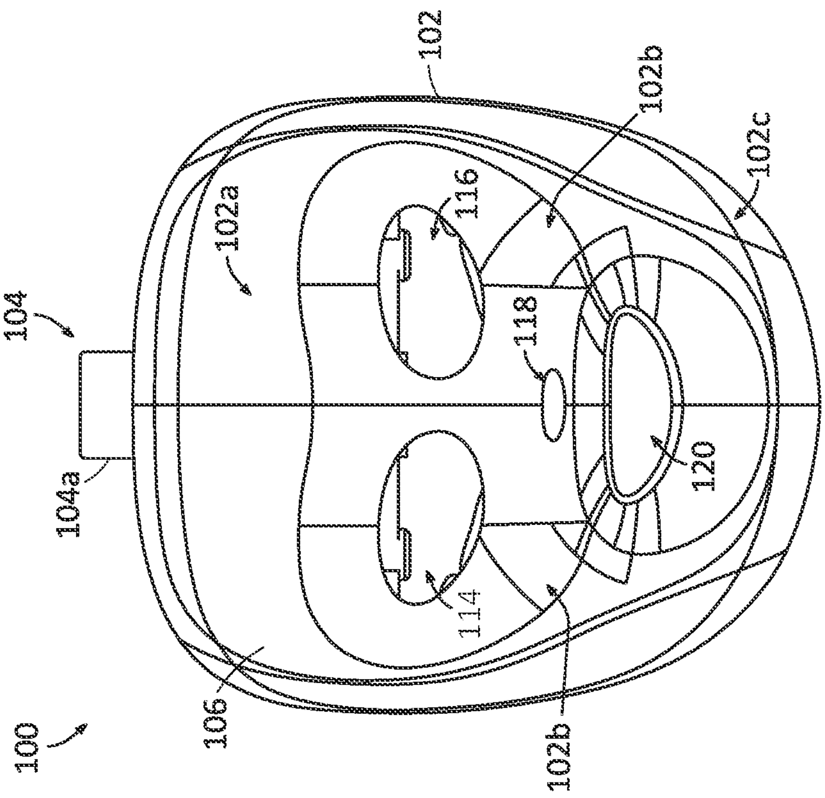
FIG. 1B is a front view of the face covering device of FIG. 1A.
Figure 1C:
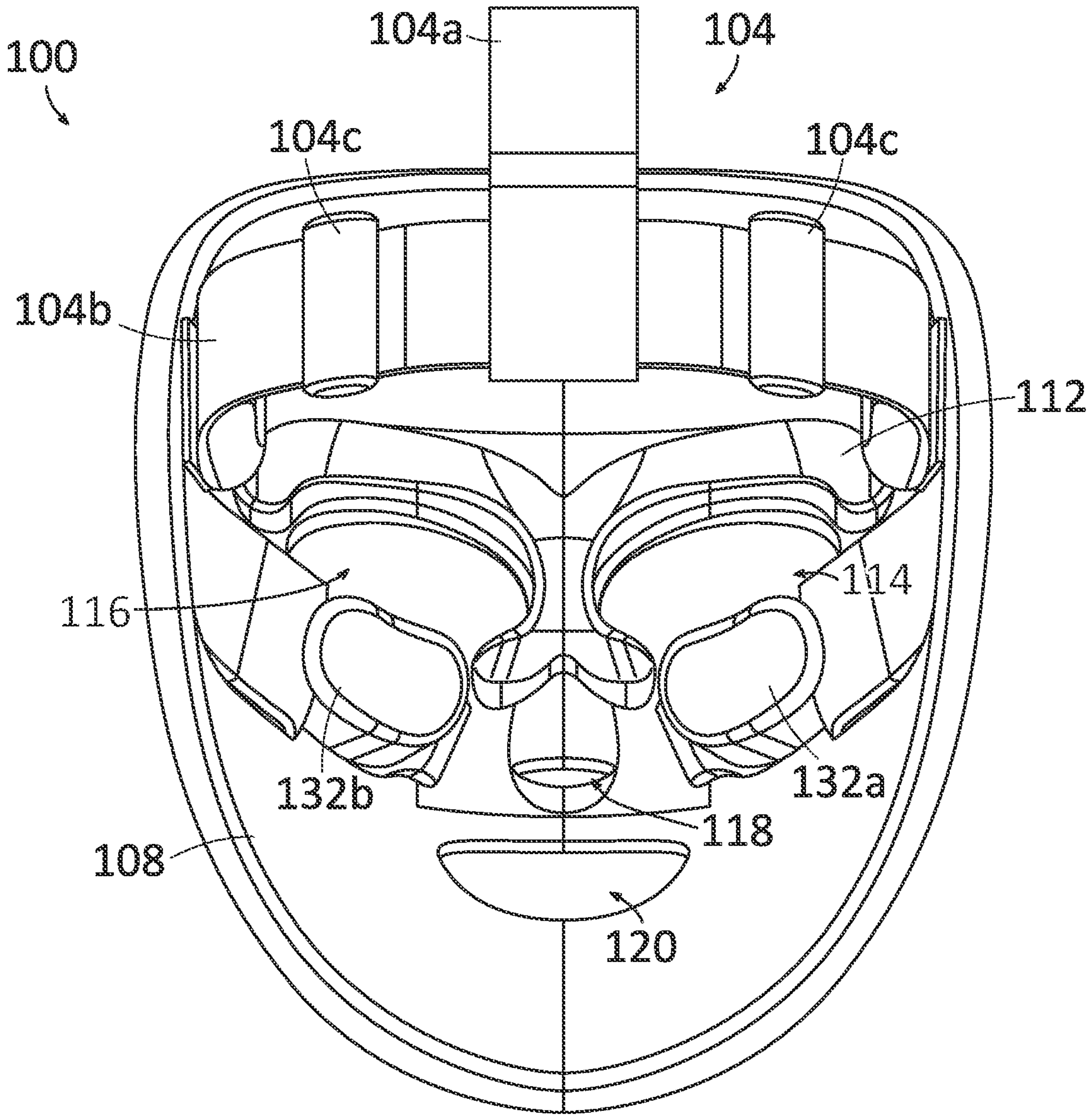
FIG. 1C is a rear view of the face covering device of FIG. 1A.

FIGS. 1A-1C illustrate one exemplary implementation of a face covering device 100 configured to provide light therapy to a user wearing the face covering device 100. The face covering device 100 in this illustrated implementation is also configured to provide cooling therapy. As mentioned above, the methods, systems, and devices described herein also apply to face covering devices that are configured to provide cooling therapy without being configured to provide light therapy.

The mask 100 includes a base 102 and a support 104 attached to the base 102. The base 102 is configured to be worn over a user's face. The support 104 is configured to be worn on the user's head to support the mask 100, and thus the base 102, on the user's head.

The support 104 can have a variety of configurations. For example, the support 104 can include a cap configured to be worn on a user's head similar to a hat. For another example, as in this illustrated implementation, the support 104 can include a strap assembly including a first strap **104*a* and a second strap 104*b* attached to the first strap 104*a*. The first strap 104*a* is an upper portion of the strap assembly and is configured to be worn over and extend front-back along a crown of a user's head. The second strap 104*b* is a lower portion of the strap assembly and is configured to be worn around and extend substantially horizontally along a partial circumference of the user's head. The second strap's extension may not be precisely horizontal but nevertheless be considered to be substantially horizontal, depending on a particular user's head and how a user positions the second strap 104*b*. In an exemplary implementation, the first strap 104*a* and the second strap 104*b* are made from a flexible material, e.g., a textile, a plastic, or a combination thereof, which may help the first strap 104*a* and the second strap 104*b*** comfortably conform to a size and shape of particular user's head.

In some implementations, the strap assembly includes padding, e.g., foam, air pockets, or other padding, configured to be positioned between the user's head and each of the strap assembly's straps **104*a*, 104*b*** to provide increased user comfort.

The strap assembly includes an adjustment mechanism **104*c*, such as a buckle (as in this illustrated implementation in which the adjustment mechanism 104*c* includes a pair of buckles), snaps, Velcro, or other adjustment mechanism, configured to allow manual user adjustment of the first strap 104*a* and the second strap to help fit the mask 100** snugly and comfortably on the user. In other implementations, the strap assembly is self-adjusting, such as by straps of the strap assembly being elastic members similar to an elastic headband.

Figure 2A:
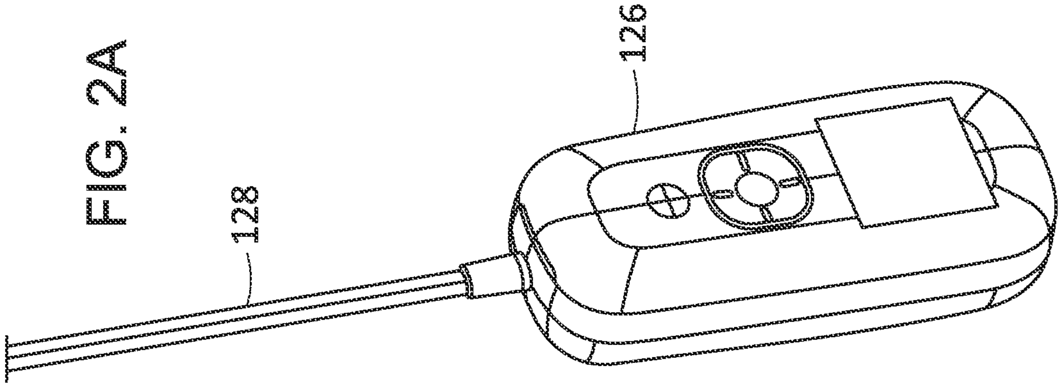
FIG. 2A is a perspective view of one implementation of a control unit configured to operably couple with the face mask of FIG. 1A.
Figure 2:
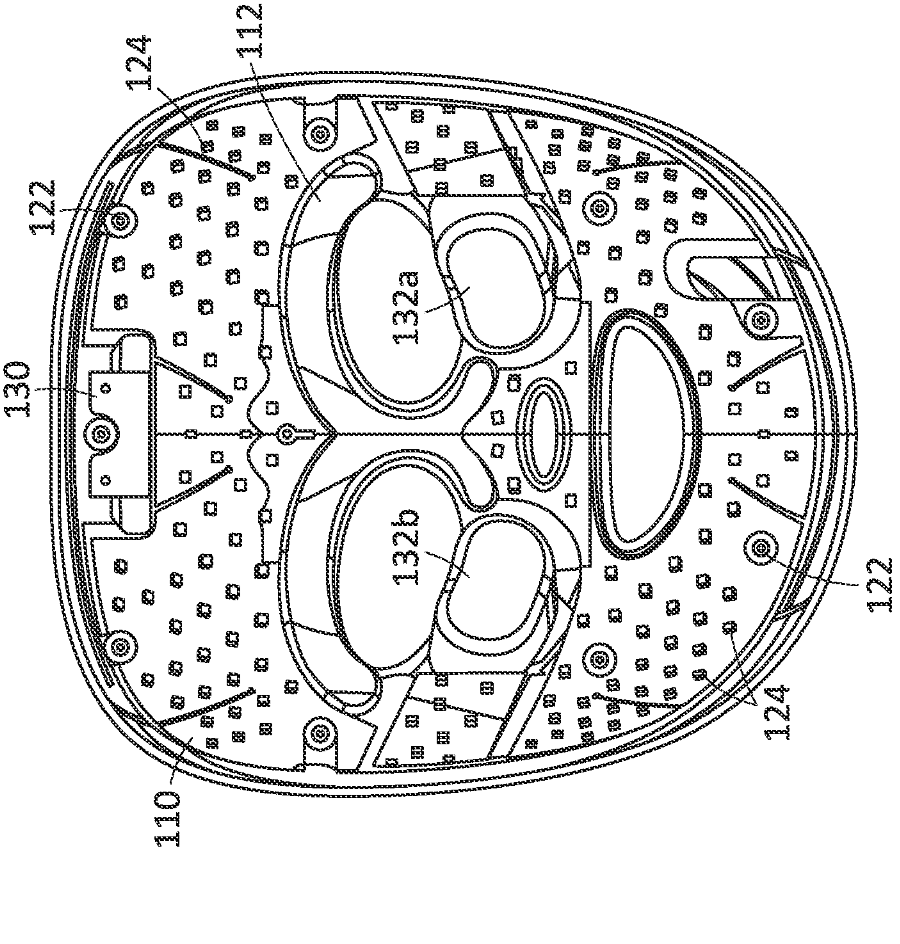
FIG. 2 is a rear view of a portion of the face covering device of FIG. 1A.

As shown in FIGS. 1A-2, the base 102 includes an outer shell 106, an inner shell 108, and an intermediate shell 110 located between the outer and inner shells 106, 108. In an exemplary implementation, the base 102 is made from a rigid material, e.g., a plastic, a metal, or a combination thereof, which may help prevent the mask 100 from bending, deflecting, twisting, or otherwise breaking and/or may help the mask's support assembly 112 be positioned predictably and securely on a face of the a user wearing the mask 100. The support assembly 112 is discussed further below. Based on a thickness and/or density of the rigid material, the mask 100 may have a relatively low weight so as to not feel uncomfortably heavy on the user's head and avoid other discomfort for the user, such as neck pain and/or compression of the user's forehead, nose, or checks.

The base 102 has a smooth outer surface and rounded edges. The smooth outer surface and rounded edges are configured to avoid risks associated with cutting, abrading, or otherwise injuring a user before, during, and after use of the mask 100.

The base 102 has a plurality of openings 114, 116, 118, 120 formed therein that each corresponds to a face feature and is configured to align at least partially with the face feature when the mask 100 is worn by a user. In this way, with a user wearing the mask 100, each of the plurality of openings 114, 116, 118, 120 will align at least partially with a feature of the user's face. Each of the plurality of openings 114, 116, 118, 120 is formed through all of the outer, inner, and intermediate shells 106, 108, 110. The plurality of openings include a first eye opening 114 configured to align at least partially with a right eye of a user wearing the mask 100, a second eye opening 116 configured to align at least partially with a left eye of the user wearing the mask 100, a nose opening 118 configured to align at least partially with a nose of the user wearing the mask 100, and a mouth opening 120 configured to align at least partially with a mouth of the user wearing the mask 100. The first and second eye openings 114, 116 are configured to allow the user to see while wearing the mask 100 without the mask 100 preventing the user from being able to see anything except an inside surface of the mask 100, e.g., an inside surface of the inner shell 108. The nose opening 118 is configured to allow the user to easily use through their nose, e.g., for breathing, etc., while the user is wearing the mask 100. The mouth opening 120 is configured to allow the user to easily use their mouth, e.g., for breathing, drinking, eating, etc., while the user is wearing the mask 100.

All of the plurality of openings 114, 116, 118, 120 in this illustrated implementation are unobstructed openings. In other implementations, one or more of the plurality of openings 114, 116, 118, 120 can be at least partially obstructed, such as with mesh, a transparent polymer plate, or other obstruction element.

The base 102 in this illustrated implementation is configured to cover substantially all of a user's face with the user wearing the mask 100. The base 102 may not entirely cover a particular user's face depending on a size and shape of the particular user's face, but the base 102 has a size configured to cover faces of most potential users of the mask 100. In this illustrated implementation, the base 102 includes a forehead portion 102*a* configured to cover at least a portion of a user's forehead with the user wearing the mask 100, a cheek portion 102*b* configured to cover at least a portion of a user's cheeks with the user wearing the mask 100, and a chin portion 102*c* configured to cover at least a portion of a user's chin with the user wearing the mask 100.

The base 102 includes openings 114, 116, 118, 120 for all of the user's eyes, nose, and mouth. In some implementations, the base 102 is configured to partially cover a user's face, such as only cover an upper half of a user's face, only cover a lower half of a user's face, cover a user's face except for left and right cheeks, or other partial coverage configuration. In such implementations, the base 102 may not have at least one of the eye, nose, and mouth openings 114, 116, 118, 120 or at least one of the forehead, cheek, and chin portions 102*a*, 102*b*, 102*c* depending on where the mask 100 is intended to be placed over a user's face.

The outer shell 106 defines an exterior surface of the mask 100 that faces away from a user's face with the user wearing the mask 100. The inner shell 108 defines an interior surface of the mask 100 that faces toward a user's face with the user wearing the mask 100. The intermediate shell 110 is sandwiched between the outer and inner shells 106, 108. FIG. 2 illustrates a plurality of interior connection points 122 at which the outer, inner, and intermediate shells 106, 108, 110 are configured to be securely attached together, such as by using pins, adhesive, welding, etc. The illustrated mask 100 includes eight interior connection points 122, but another number of interior connection points 122 can be used.

A light assembly is located on the intermediate shell 110. The light assembly is configured to apply light therapy, such as one or more of an anti-aging treatment and an anti-breakout treatment, to a user wearing the mask 100. The light assembly includes a plurality of lights 124 spaced apart from one another in a pattern, e.g., a grid pattern, a random pattern, or other pattern, on the intermediate shell 110. For example, the plurality of lights 124 can be positioned in a grid pattern with substantially even spacing between adjacent lights 124. In another example, the plurality of lights 124 can be positioned in a random pattern with uneven spacing between adjacent lights 124. In yet another example, the plurality of lights 124 can be positioned in a pattern with a mixture of even and uneven spacing of adjacent lights 124.

In this illustrated implementation, the plurality of lights 124 are positioned in a grid pattern on an inner surface of the intermediate shell 110 that is configured to face toward a user's face with the user wearing the mask 100. For example, the substantially even spacing between adjacent lights 124 can be a distance of a value in a range between about 1 mm and about 20 mm, including all values and sub-ranges therein. The spacing between adjacent lights 124 corresponds to an effectiveness of a light therapy provided by the plurality of lights 124. That is, decreasing the spacing between adjacent lights 124 increases the effectiveness, and increasing the spacing between adjacent lights 124 decreases the effectiveness. Therefore, the spacing between the lights 124 corresponds to the desired efficacy of the light therapy.

Each of the lights 124 requires power to operate, as discussed further below. Therefore, increasing the quantity of lights 124 increases the amount of power required to operate the light assembly. It may therefore be desirable in some circumstances for the mask 100 to include fewer lights 124 to decrease power requirements of the mask 100.

During use, the plurality of lights 124 are configured to emit heat in addition to emitting light. The heat emitted by the plurality of lights 124, however, is not so great so as to cause injury or other damage to the user during use. Decreasing the spacing between adjacent lights 124 causes a local concentration of thermal energy (e.g., heat). Therefore, none of the lights 124 are immediately adjacent to one another, e.g., each of the lights 124 is at least a minimum distance away from each of the light(s) 124 adjacent thereto, so avoid heat concentration. In an exemplary implementation, the minimum distance is about 1 mm.

Each of the lights 124 is configured to emit light at a predetermined wavelength configured to facilitate various light therapies, such as one or more of an anti-aging treatment and an anti-breakout treatment. The predetermined wavelength can be, for example, a wavelength in a range between about 300 nm and about 1000 nm. The light emitted by the plurality of lights 124 is configured to reach one or more layers of skin, e.g., an epidermis, a dermis, and/or a hypodermis, of a user wearing the mask 100. The layer(s) of skin reached by the light corresponds to the wavelength. For example, a longer wavelength of light is configured to reach a deeper layer of skin than a shorter wavelength of light. In some implementations, the wavelength emitted by the lights 124 is configured to be adjustable, such as by one or more of a user manually selecting the wavelength and a wireless computing device configured to wirelessly communicate with a controller of the face covering device 100 to allow a user to manually select the wavelength.

The light 124 are configured to be selectively turned on by a user, to provide the light therapy, and off by the user, to not be providing the light therapy. The lights 124 are light emitting diodes (LEDs) in this illustrated implementation. A number of the lights 124 can be, for example, in a range between ten and two hundred; in a range between fifty and one hundred fifty; in a range between sixty and one hundred; in a range between seventy-five and eighty-five; fifty; seventy-five; eighty; eighty-five; or other number.

As shown in FIG. 2A, a control unit 126 is configured to be operably coupled to the mask 100. The control unit 126 is configured to allow a user to control various functions of the mask 100. The control in this illustrated implementation includes control of the light therapy (e.g., turning the lights 124 on/off, adjusting light brightness, controlling light color, and adjusting light wavelength), control of the cooling therapy (e.g., turning cooling therapy on/off and adjusting cooling strength), and power control (e.g., controlling current and/or voltage of an electrical signal provided by a power source). The control unit 126 is configured to be connected to the mask 100 with a cable 128. FIG. 2A shows the cable 128 connected at one end of the cable 128 to the control unit 126. The other, opposite end of the cable 128 is configured to be connected to the mask 100. In an exemplary implementation, the cable 128 is configured to be fixedly connected to the mask 100, which may help prevent loss of the control unit 126.

The control unit 126 in this illustrated implementation is a dedicated control unit for the mask 100 and thus cannot control other masks 100 or other devices. In other implementations, the control unit 126 is a dedicated control unit for the mask 100 but is a wireless remote control connected wirelessly to the mask 100, e.g., via Bluetooth or other wireless communication protocol. In still other implementations, the control unit 126 is not a dedicated control unit for the mask 100 and can control other masks and/or other devices. Examples of non-dedicated control units include a mobile phone, a mobile tablet, and other computing devices configured to wirelessly communicate with the mask 100.

The control unit 126 includes a power source (obscured in FIG. 2A), such as a battery or other power source, configured to provide power to the lights 124 of the mask 100 and to a cooling system of the mask 100. The control unit 126 including the power source may help reduce a weight and/or bulkiness of the mask 100, which may provide for a better user experience. In other implementations, the mask 100 includes a power source instead of or in addition to the control unit 126.

The mask 100 includes a controller (e.g., a processor, a microcontroller, or other electronic controller) configured to be in operable communication with the control unit 126. In an exemplary implementation, the mask 100 includes a printed circuit board (PCB) 130 that includes the controller. FIG. 2 illustrates one example location of the PCB 130 on an exterior surface of the intermediate shell 110, e.g., a surface facing away from a user's face with the user wearing the mask 100, but the PCB 130, and thus the controller, can be secured to the mask 100 elsewhere. FIG. 2 shows the PCB 130 in an upper portion of the mask 100 in a forehead area of the mask 100. Because of the relatively large amount of surface area in the forehead area of the mask 100, the PCB 130 being located in the upper portion may allow for a larger, and thus more powerful, controller and associated PCB components (e.g., memory, bus, transceiver or other wireless communication unit, etc.). For another example, the PCB 130 can be located in a lower portion of the mask 100 in a chin area of the mask 100. In an exemplary implementation, the cable 128 extends from the lower portion of the mask 100, so the PCB 130 being in the lower portion may ease manufacturing of the mask 100 for operable coupling of the control unit 126 and the controller.

In some implementations, the control unit 126 includes the PCB, and thus the controller, instead of the mask 100.

The mask 100 includes first and second undereye supports 132*a*, 132*b* configured to provide support for the mask 100 against the user's face by contacting or otherwise sitting against the user's cheeks and/or cheek bones to facilitate the support. That is, the user's cheeks and/or cheek bones may contribute a resistive force that prevents the face mask 100 from moving relative to the user's face.

The first undereye support 132*a* is located under the first eye opening 114 and is thus configured to be positioned below a right eye of a user wearing the mask 100. The second undereye support 132*b* is located under the second eye opening 116 and is thus configured to be positioned below a left eye of a user wearing the mask 100. The first and second undereye supports 132*a*, 132*b* are each configured to contact a region under its associated eye of the user wearing the mask 100. The illustrated mask 100 includes two undereye supports 132*a*, 132*b*, but another number is possible, e.g., one, three, etc.

As mentioned above, the mask 100 includes a cooling system configured to provide cooling therapy to a user wearing the mask 100, such as one or more of an anti-aging treatment and an anti-breakout treatment. As in this illustrated implementation, the cooling function can correspond to a cooling effect facilitated passively and/or actively by the first and second undereye supports 132*a*, 132*b*. For example, coolness generated by the mask 100, e.g., by the mask's cooling system, can be configured to flow through the undereye supports 132*a*, 132*b* to provide cooling therapy to the user's face during wear of the mask 100. As mentioned above, the mask 100 includes a cooling system configured to provide the cooling therapy to a user wearing the mask 100, such as one or more of an anti-aging treatment and an anti-breakout treatment. Cooling systems for face covering devices are further discussed, for example, in U.S. patent application Ser. No. 18/411,644 entitled "Face Masks With Noise Attenuation" filed on Jan. 12, 2024, which is hereby incorporated by reference in its entirety.

As mentioned above and as shown in FIG. 2, the face mask 100 includes a support assembly 112 configured to help support the face mask 100 on the user's face. The support assembly 112 is also configured to protect the user's eyes from the light emitted by the plurality of lights 124 by preventing lights emitted from the plurality of lights 124 from passing through the first and second eye openings 114, 116 so as to prevent light from entering either of the user's eyes with the user wearing the mask 100. The support assembly 112 is shown as a standalone member in FIGS. 3A-3D.

In general, the support assembly has a shape that follows a shape of eyebrows, an inner side of a left eye, an inner side of a right eye, and a nose. The support assembly 112 includes a pair of eyebrow supports 310, 312 and/or one or more nose supports 314, 318, 320. In an exemplary implementation, as in this illustrated implementation, the support assembly 112 includes a pair of eyebrow supports 310, 312 and one or more nose supports 314, 318, 320, which may help provide more support for a full-face mask such as the illustrated mask 100 than when the support assembly 112 includes a pair of eyebrow supports but no nose supports or includes one or more nose supports but no eyebrow supports. In implementations of the mask 100 in which the base 102 is configured to partially cover a user's face, the mask 100 may omit a portion of the mask 100 where the support assembly 112 could provide support and thus not include those aspects of the support assembly, such as a mask 100 omitting a portion configured to overlie a user's eyebrows and thus not including any eyebrow supports.

Figure 3A:
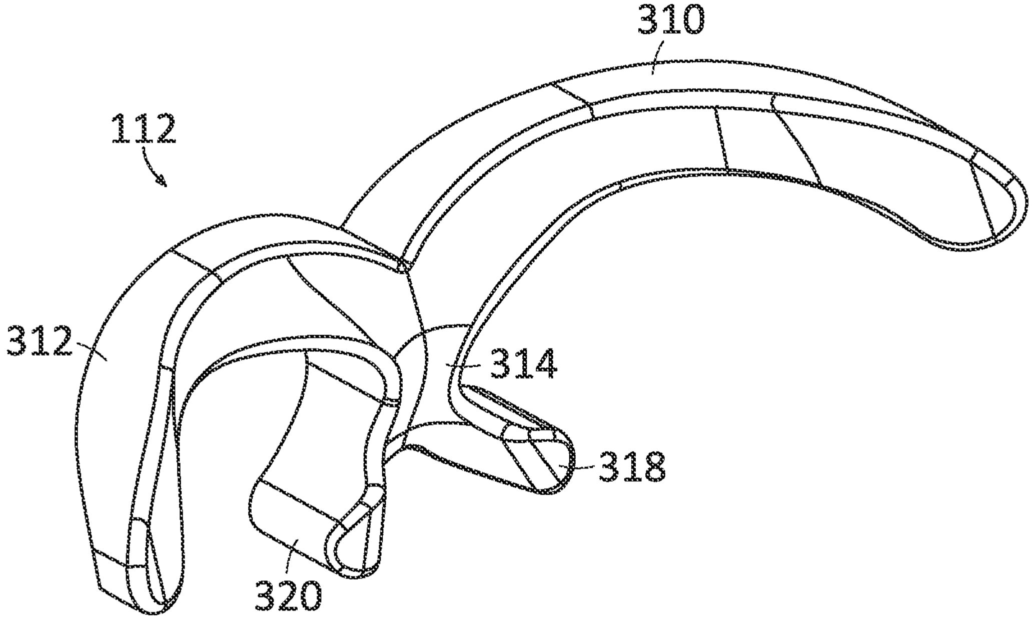
FIG. 3A is a perspective view of a support assembly of the face covering device of FIG. 1A.
Figure 3B:
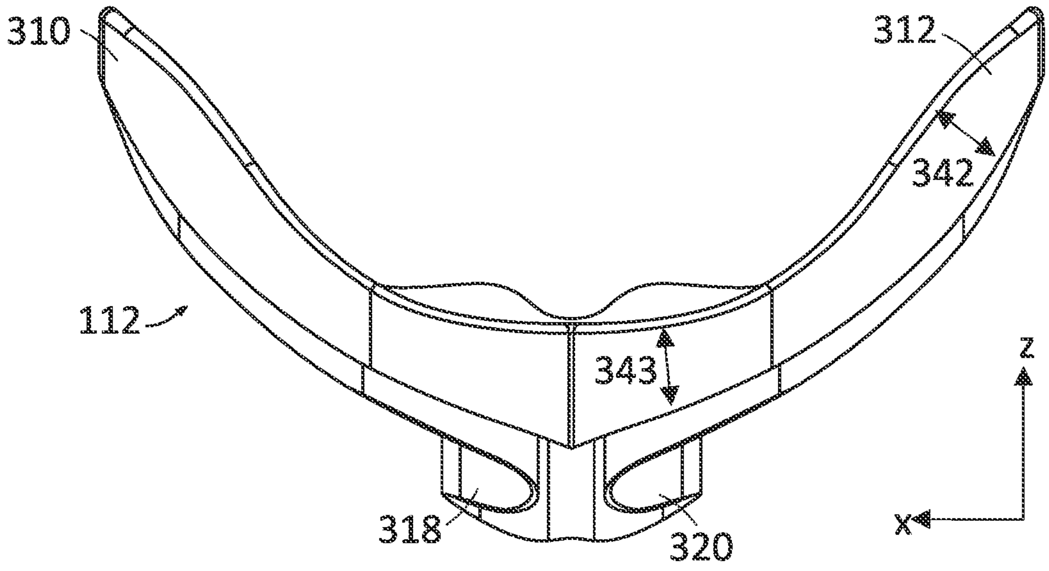
FIG. 3B is another perspective view of the support assembly of FIG. 3A.

The pair of eyebrow supports 310, 312 are configured to contact a user's eyebrows and/or orbital bones with the user wearing the mask 100, such that the user's eyebrows and/or orbital bones contribute to a resistive force that prevents the face mask 100 from moving relative to the user's face. The support assembly 112 in this illustrated implementation includes a first eyebrow support 310 located above the first eye opening 114 and configured to align and contact at least partially with a right eyebrow of a user wearing the mask 100 and a second eyebrow support 312 located above the second eye opening 116 and configured to align and contact at least partially with a left eyebrow of the user wearing the mask 100. The eyebrow supports 310, 312 are thus configured to surround an upper portion of the user's eyes. As shown in FIGS. 3A and 3D, the first and second eyebrow supports 310, 312 are attached to one another in a central, upper area of the support assembly 112 above the one or more nose supports 314, 318, 320.

The one or more nose supports 314, 318, 320 are configured to contact a user's nose, e.g., a bridge and/or sides of the user's nose, such that the user's nose contributes to the resistive force that prevents the face mask 100 from moving relative to the user's face. The support 104 also contributes to the resistive force. As in this illustrated implementation, the nose support can include a nose bridge support 314, a first nostril support 318, and a second nostril support 320. The nose bridge support 314 configured to align and contact at least a portion of a bridge of a nose of a user wearing the mask 100, a first nostril support 318 configured to align above and contact at least partially with a right ala (right base wing) of the user wearing the mask 100, and a second nostril support 320 configured to align above and contact at least partially with a left ala (left base wing) of the user wearing the mask 100. The eyebrow supports 310, 312 are thus configured to surround an inner portion of the user's eyes. The one or more nose supports 314, 318, 320 are located above the nose opening 118, which is configured to align with the nose's nostrils, and laterally inward of their respective eye openings 114, 116, e.g., the first nostril support 318 is located laterally inward of first eye opening 114 and the second nostril support 320 is located laterally inward of the second eye opening 116.

The nose bridge support 314 is centrally positioned with respect to the first and second eyebrow supports 310, 312 and the first and second nostril supports 318, 320. The first eyebrow support 310 is integrally formed with and extends laterally outward from a first side of the nose bridge support 314, e.g., laterally to the right from a right side of the nose bridge support 314, and the second eyebrow support 312 is integrally formed with and extends laterally outward from a second side of the nose bridge support 314, e.g., laterally to the left from a left side of the nose bridge support 314. Therefore, a first eye support opening 370 is defined by an inner surface of each of the first eyebrow support 310 and the nose bridge support 314 e.g., on the right side of the nose bridge support 314, and a second eye support opening 372 is defined by an inner surface of each of the second eyebrow support 312 and the nose bridge support 314 e.g., on the left side of the nose bridge support 314. The first and second eye support openings 370, 372 are aligned with the first and second eye openings 114, 116, respectively, and are thus configured to align at least partially with eyes of a user wearing the mask 100. The user's vision through the first and second eye openings 114, 116 is thus not obstructed by the support assembly 112. A combination of the first eyebrow support 310 and the nose bridge support 314 define a first eye support. A combination of the second eyebrow support 312 and the nose bridge support 314 define a second eye support.

The support assembly 112 is configured to form a seal against the face of the user wearing the face mask 100 such that, with the plurality of lights 124 activated so as to be emitting light, the support assembly 112 facilitates the blocking of light from the user's eyes. The first eye support, e.g., the first eyebrow support 310 and the nose bridge support 314, are configured to prevent light from the first eye support opening 370, and the second eye support, e.g., the second eyebrow support 312 and the nose bridge support 314, is configured to prevent light from entering the second eye support opening 372.

At least a portion of the support assembly 112 is made from an opaque material, such as rubber, plastic, foam (e.g., polyethylene), or combination thereof, configured to inhibit or otherwise prevent light from traveling therethrough. In some implementations, all of the first and second eyebrow supports 310, 312, the nose bridge support 314, and the first and second nostril supports 318, 320 are each made from an opaque material (same or different from one another). In some implementations, not all of the first and second eyebrow supports 310, 312, the nose bridge support 314, and the first and second nostril supports 318, 320 are each made from an opaque material (same or different from one another). Any of the first and second eyebrow supports 310, 312, the nose bridge support 314, and the first and second nostril supports 318, 320 that are not made from an opaque material in full or in part can nevertheless be configured to block light as described herein, such as by non-opaque portion(s) thereof not being along a light pathway.

In some implementations, regardless of whether or not any one or more of the first and second eyebrow supports 310, 312, the nose bridge support 314, and the first and second nostril supports 318, 320 are made in full or in part from an opaque material, the support assembly 112 can include a protective coating thereon. The protective coating is at least one layer of material that surrounds the first and second eyebrow supports 310, 312, the nose bridge support 314, and the first and second nostril supports 318, 320. The protective coating is made from an opaque material, such as silicone or other plastic, a textile, or other non-porous material configured to be safely against a user's skin, configured to inhibit or otherwise prevent light from traveling therethrough. The protective coating being non-porous allows the protective coating, and thus the underlying first and second eyebrow supports 310, 312, the nose bridge support 314, and the first and second nostril supports 318, 320, to not absorb sweat, oils, or any other liquid when the mask 100 is worn by a user.

In an exemplary implementation, the first and second eyebrow supports 310, 312, the nose bridge support 314, and the first and second nostril supports 318, 320 are made from foam (e.g., polyethylene or other foam), gel, or other compressible material, and the protective coating is silicone. The protective coating being silicone may facilitate easy cleaning of the support assembly 112, e.g., by wiping the support assembly 112 after use, and/or may help the support assembly 112 grip a user's face to discourage slippage. The first and second eyebrow supports 310, 312, the nose bridge support 314, and the first and second nostril supports 318, 320 being made from a compressible material provides padding and allows the support assembly 112 to dynamically conform to a user's face, thereby allowing the support assembly 112 to provide a seal against the user's face regardless of the particular size and shape of the face of the user wearing the face mask. Therapy may thus be provided by the face mask while the face mask is comfortably positioned on the user's face and the user avoids direct exposure of light into their eyes. Materials other than foam may provide similar functionality, such as gel packs.

In some implementations, regardless of whether or not any one or more of the first and second eyebrow supports 310, 312, the nose bridge support 314, and the first and second nostril supports 318, 320 are made in full or in part from an opaque material, and regardless of whether or not the support assembly 112 includes a protective coating, the support assembly 112 can surround at least a portion of each of the user's eyes such that light emitted from the lights 124 is blocked from reaching the user's eyes when the user is wearing the face covering device 100.

As in this illustrated implementation, as shown in FIG. 3D, the second eyebrow support 312 can have a width 354 that is equal to or greater than a maximum width of a typical adult eyebrow (for masks intended for adult use) and has a length 352 that corresponds to a length of that is equal to or greater than a maximum width of a typical adult human eye (for masks intended for adult use). The length 352 can be, for example, in a range between about 10 mm and about 20 mm. For another example, the length 352 can be about 15 mm. The first eyebrow support 310 has a same width 354 and length 352 as the second eyebrow support 312. Accordingly, light emitted by the subset of the plurality of lights 124 positioned in the forehead portion 102*a* of the base 102 is configured to be blocked by the first and second eyebrow supports 310, 312 and thus prevent the light from reaching eyes of a user wearing the mask 100. As also shown in FIG. 3D, the nose bridge support 314 has a length 356 that corresponds to a length of a typical adult human eye (for masks intended for adult use). The length 356 can be, for example, in a range between about 10 mm and about 20 mm. For another example, the length 356 can be about 17 mm.

Heights of various portions of the support assembly 112 can be the same or different from one another. As shown in this illustrated implementation in FIG. 3C, the second nostril support 320 has a first height 340, which is also the height of the first nostril support 318, and the nose bridge support 314 has a fourth height 346 and a fifth height 347. In an exemplary implementation, the first height 340 is in a range between about 5 mm and about 15 mm, such as about 10 mm. As shown in FIG. 3B, the second eyebrow support 312 has a second height 342 in an outer portion thereof and a third height 343 in an inner portion thereof that is radially inward of the outer portion in a direction toward the nose bridge support 314. The first eyebrow support 310 has the same second and third heights. Each of the second and third heights 342, 343 can be in a range between about 10 mm and about 40 mm. In some implementations, the height of the first and second eyebrow supports 310, 312 tapers outwardly from larger to smaller, which may help support the support assembly 112 on a user's face. For example, the second height 342 can be about 15 mm and the third height 343 can be about 37 mm. The fourth height 346 of the nose bridge support 314 corresponds to the portion of the nose bridge support 314 adjacent the first and second nostril supports 318, 320, and the fifth height 347 of the nose bridge support 314 corresponds to the portion of the nose bridge support 314 adjacent the first and second eyebrow supports 310, 312. In an exemplary implementation, each of the fourth and fifth heights 346, 347 is in a range between about 30 mm and about 40 mm, for example the fourth height 346 being about 35 mm and the fifth height 347 being about 37 mm.

The support assembly 112 includes angled portions and curves configured to contour to a user's face. The dimensions and curves of the support assembly 112, alone or in combination with the compressible material forming the first and second eyebrow supports 310, 312, the nose bridge support 314, and the first and second nostril supports 318, 320 of the support assembly 112, may help ensure that the support assembly 112 matches contours of a face of any user wearing the mask 100 and may thus to avoid any pinching and/or bruising of the user.

Figure 3C:
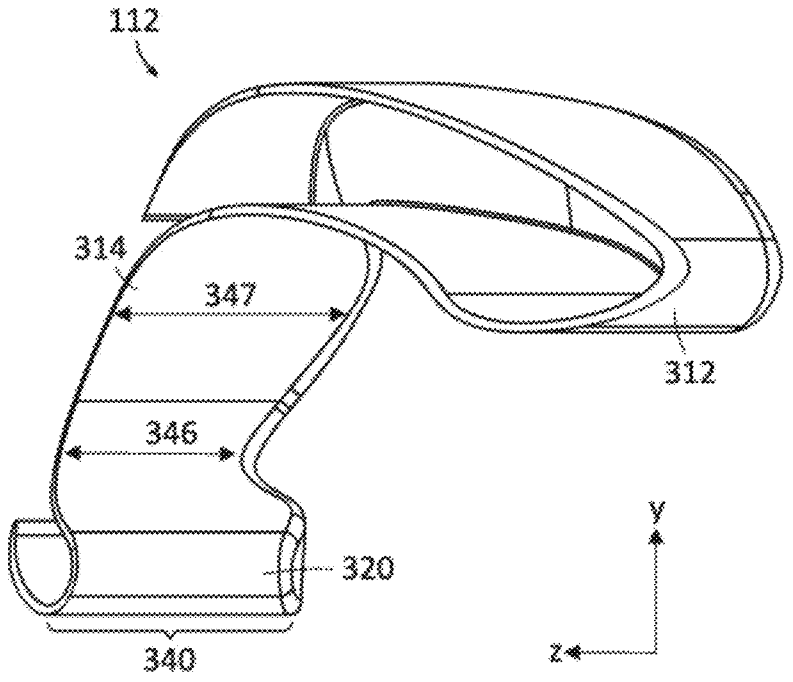
FIG. 3C is yet another perspective view of the support assembly of FIG. 3A.
Figure 3D:
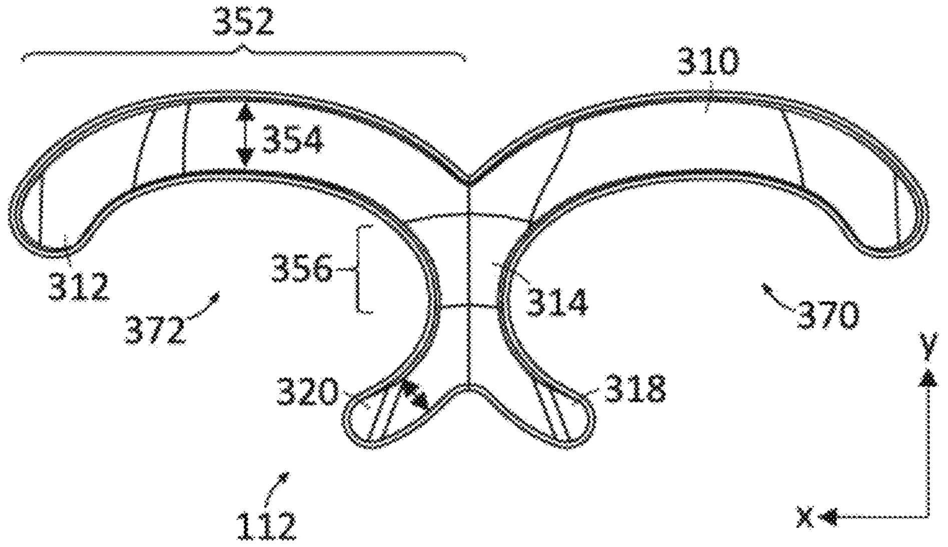
FIG. 3D is still another perspective view of the support assembly of FIG. 3A.

As shown in FIG. 3C, the nose bridge support 314 extends at an angle in a z-y plane. The angle of the nose bridge support 314 corresponds to an angle of a typical adult human nose (for masks intended for adult use), such as in a range between about 10 degrees and about 60 degrees. The first and second eyebrow supports 310, 312 each has at least one radius of curvature that corresponds to a typical adult human bone structure (for masks intended for adult use). As shown in FIG. 3B, the first and second eyebrow supports 310, 312 each has a first radius of curvature in an x-z plane. As shown in FIG. 3D, the first and second eyebrow supports 310, 312 each has a second radius of curvature in an x-y plane. The first and second nostril supports 318, 320 each has a third radius of curvature in the x-y plane. The third radius of curvature corresponds to a typical adult human bone structure (for masks intended for adult use).

The support assembly 112 is configured to maintain the plurality of light 124 at a distance from a user's face with the user wearing the mask 100, which may avoid risks associated with user exposure to any heat produced by the light assembly while in use. The dimensions and curvature of the support assembly 112 facilitate the maintenance of the distance so that there is a gap of space between the lights 124 and the user's face. The support assembly 112 has a minimum height for any portion thereof, with the minimum height corresponding to the distance between the light assembly and the user's face. The minimum height can correspond to a compressed configuration of the support assembly 112, in which the mask 100 is being worn by a user and compressible material forming at least part of the support assembly 112 is at least partially compressed, or an uncompressed configuration of the support assembly 112, in which the mask 100 is not being worn by a user. In an exemplary implementation, the minimum height of the support assembly 112 is in a range between about 5 mm and about 50 mm, for example in a range between about 10 mm and about 40 mm or in a range between about 30 mm and about 40 mm. In such an implementation, with the minimum height of the support assembly 112 being in a range between about 5 mm and about 50 mm, the distance between the plurality of lights 124 and the user's face is in a range between about 10 mm and about 40 mm.

In some implementations, the distance is the same for each of the plurality of lights 124. In other implementations, the distance of at least one light of the plurality of lights 124 is different from the distance of at least one other of the plurality of lights 124.

As mentioned above, compressible material can form the first and second eyebrow supports 310, 312, the nose bridge support 314, and the first and second nostril supports 318, 320 of the support assembly 112, with or without a protective coating surrounding the first and second eyebrow supports 310, 312, the nose bridge support 314, and the first and second nostril supports 318, 320 of the support assembly 112. By being compressible, the support assembly 112 can be configured to dynamically conform to a user's face. Any compression of the material is not so much that the base 102 directly contacts the user's face with the mask 100 on the user's face with the support 104 removably secured on the user's head. The compressible material may be covered one or more layers of the same material or a different material. For example, an inner material (e.g., the compressible material) may be covered by an outer material configured to facilitate easy cleaning by the user. For example, water or a cleaning solution can be configured to be applied to the protective coating by a user and subsequently wiped off in order to quickly and easily clean an outer surface of the support assembly 112. Accordingly, the support assembly 112 may be maintained in a hygienic state such that the face mask 100 may be repeatedly used by the same user or by different users.

The support assembly 112 is fixedly attached to the base 102, which may help ensure that the support assembly 112 aligns with a user's face as intended. The support assembly 112 is fixedly attached to the base 102 using one or more attachment mechanisms, such as an adhesive (e.g., glue, tape, etc.), a fastener (e.g., a screw, a bolt, a staple, etc.), or other attachment mechanism. For example, a first adhesive can be used to couple the compressible material of the support assembly 112 to the protective coating, and a second adhesive can be used to couple the protective coating to the base 102. For example, an adhesive can be used to couple the compressible material of the support assembly 112 to the base 102.

In other implementations, the support assembly 112 is releasably attached to the base 102, which may help facilitate cleaning of the support assembly 112 and/or replacement of the support assembly 112 without having to replace the more expensive base 102. The support assembly 112 is releasably attached to the base 102 using one or more attachment mechanisms, such as Velcro, a hook, a snap, etc.

The first and second undereye supports 132*a*, 132*b* are configured to block light similar to that discussed herein regarding the support assembly 112. Light emitted by the plurality of lights 124 positioned in the chin portion 102*c* of the base 102 is configured to be blocked by the first and second undereye supports 132*a*, 132*b* so the light does not reach either eye of a user wearing the mask 100. The first and second undereye supports 132*a*, 132*b* can have similar construction and be made from similar materials as the support assembly 112, but need not. In some implementations, the first and second undereye supports 132*a*, 132*b* are integrally formed with the support assembly 112, which may help surround an entire circumference of the user's eyes. In some implementations, the first and second undereye supports 132*a*, 132*b* are not integrally formed with the support assembly 112, which may facilitate manufacturing of the mask 100 and/or facilitate cleaning and/or replacement of the first and second undereye supports 132*a*, 132*b* separate from the support assembly 112.

In an exemplary implementation, each of the first and second undereye supports 132*a*, 132*b* has a height in a range between about 10 mm and about 40 mm, for example about 35 mm. The height of each of the first and second undereye supports 132*a*, 132*b* generally corresponds to the first height 340 of the first and second nostril supports 318, 320, which allows a contact surface of each of the first and second nostril supports 318, 320 to sit flush (e.g., coplanar) with the first and second undereye supports 132*a*, 132*b*, respectively and/or may increase the user's comfort while wearing the face covering device 100.

Figure 4A:
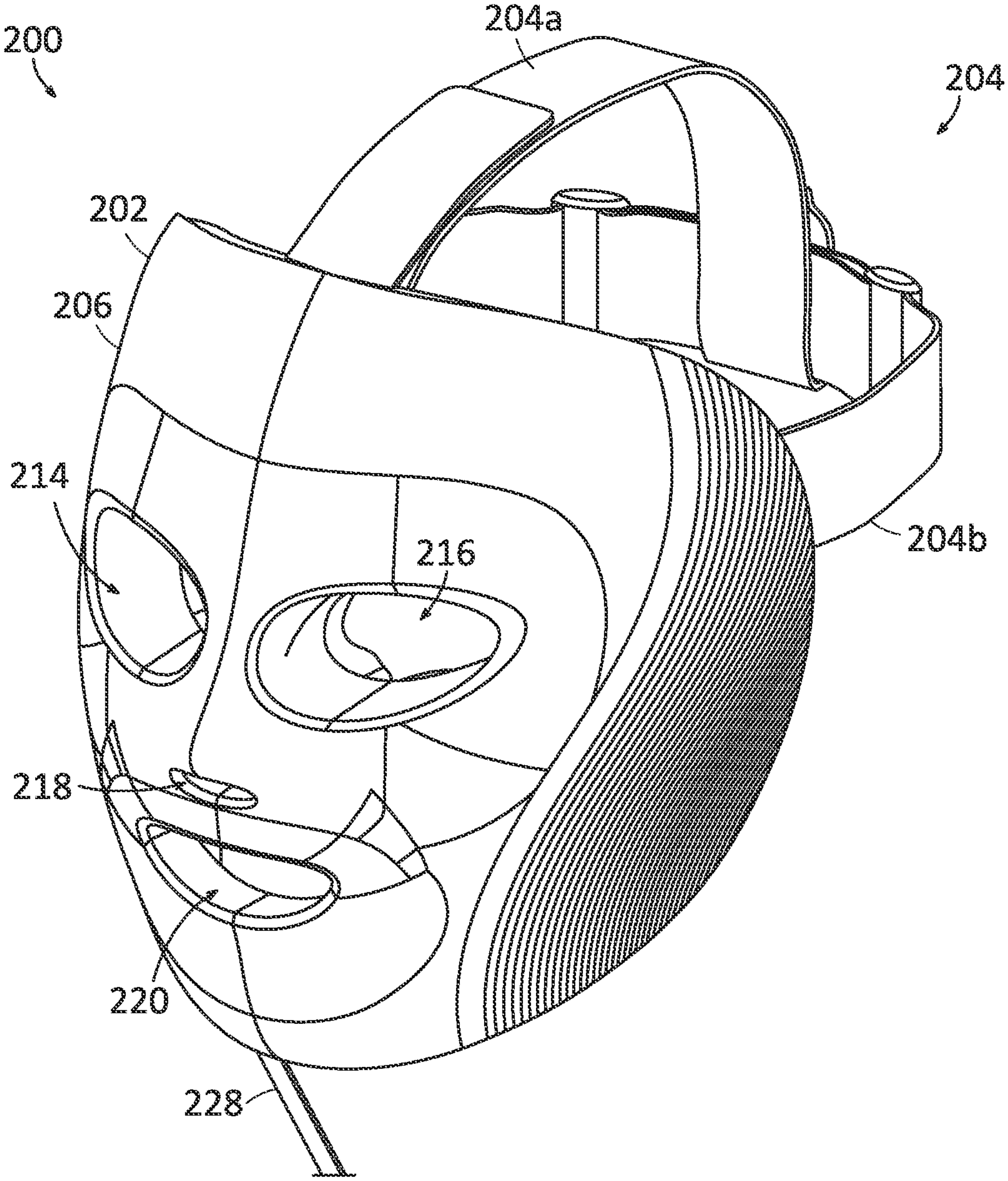
FIG. 4A is a perspective view of another implementation of a face covering device.

FIG. 4A illustrates another implementation of a face mask 200 configured to provide light therapy to a user wearing the face mask 200. The face mask 200 in this illustrated implementation is also configured to provide cooling therapy.

Figure 4B:
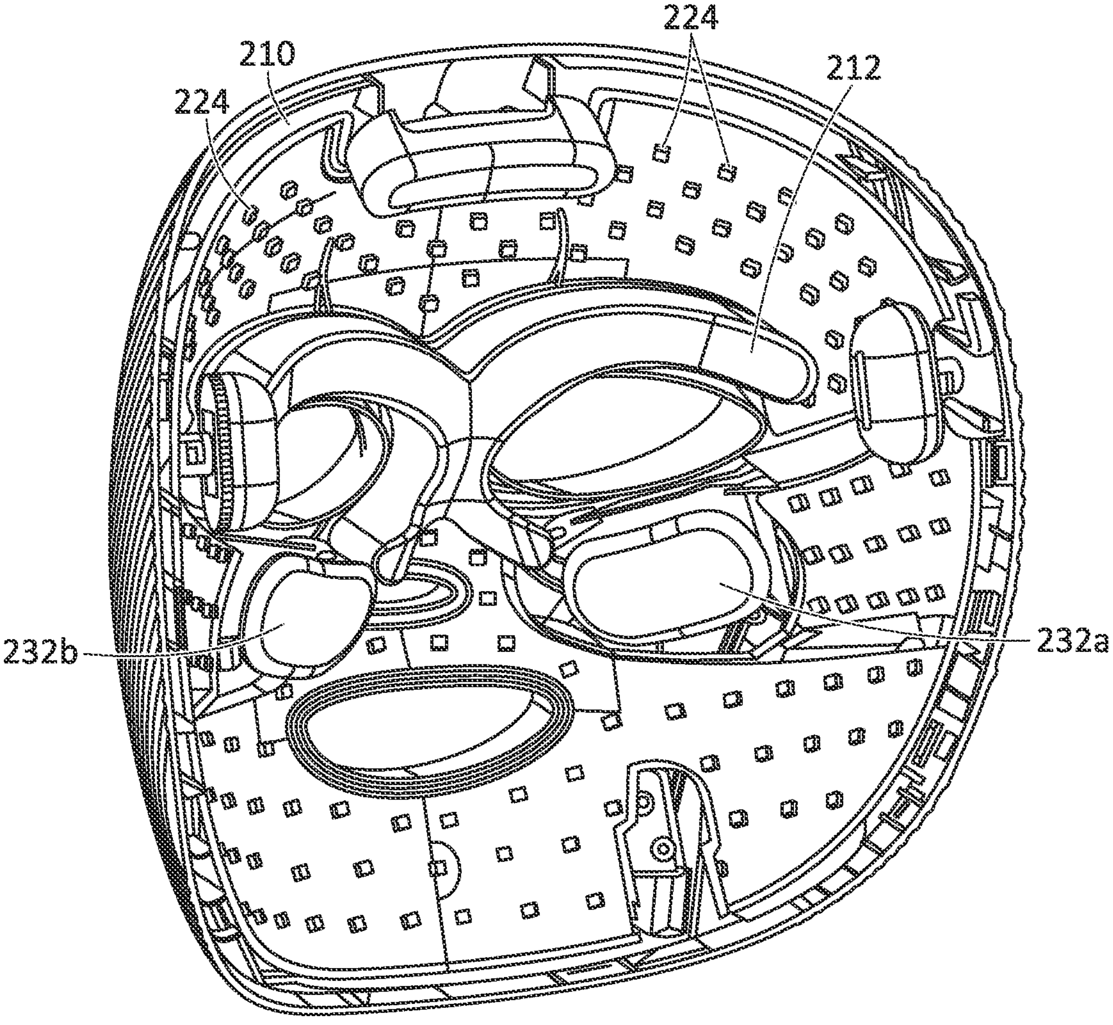
FIG. 4B is a perspective view of an intermediate shell of the face mask of FIG. 4A.
Figure 4D:
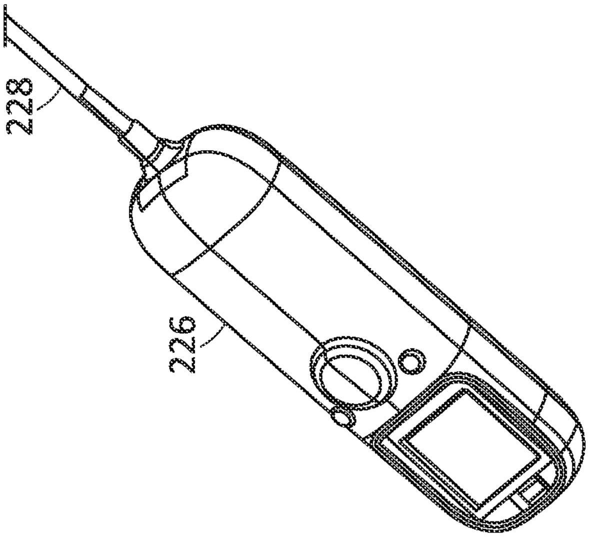
FIG. 4D is a perspective view of one implementation of a control unit operably coupled with the face mask of FIG. 4A.
Figure 4C:
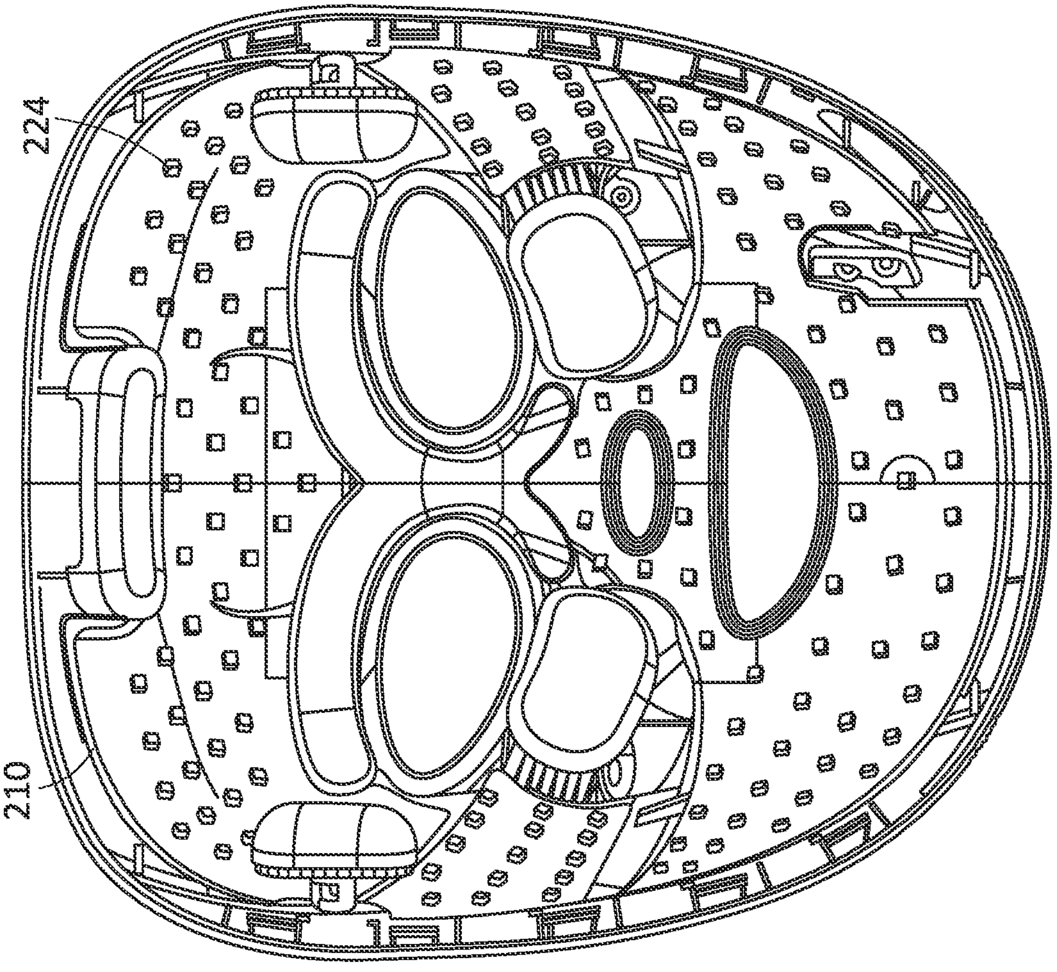
FIG. 4C is another perspective view of the intermediate shell of FIG. 4B.

The face mask 200 of FIG. 4A is generally configured and used similar to the face mask 100 of FIGS. 1A-1C and includes a base 202 including an outer shell 206, an inner shell, and an intermediate shell 210 (shown in FIGS. 4B and 4C); a support 204 including first and second straps 204*a*, 204*b*; a support assembly 212; a plurality of openings including a first eye opening 214, a second eye opening 216, a nose opening 218, and a mouth opening 220; a plurality of interior connection points (obscured in FIG. 4A); a light assembly includes a plurality of lights 224 (shown in FIGS. 4B and 4C); a PCB (obscured in FIG. 4A); a cooling system (obscured in FIG. 4A); and first and second undereye supports 232*a*, 232*b*. A control unit 226 (shown in FIG. 4D) is operably coupled with the mask 200 using a cable 228 and is generally configured and used similar to the control unit 126 of FIG. 2A.

The support assembly 212 is generally configured and used similar to the support assembly 112 of the mask 100 of FIGS. 1A-1C, e.g., includes a pair of eyebrow supports and a nose support including a nose bridge support, a first nostril support, and a second nostril support. The support assembly 212 in this illustrated implementation is configured to be fixedly attached to the base 202. As shown in FIG. 4E, the support assembly 212 includes a plurality of interior connection points 213 at which the support assembly 212 and the base 202, e.g., the outer shell 206 thereof, are configured to be securely attached together, such as by using pins, adhesive, welding, etc. The illustrated support assembly 212 includes nineteen interior connection points 213, but another number of interior connection points 213 can be used.

Figure 4F:
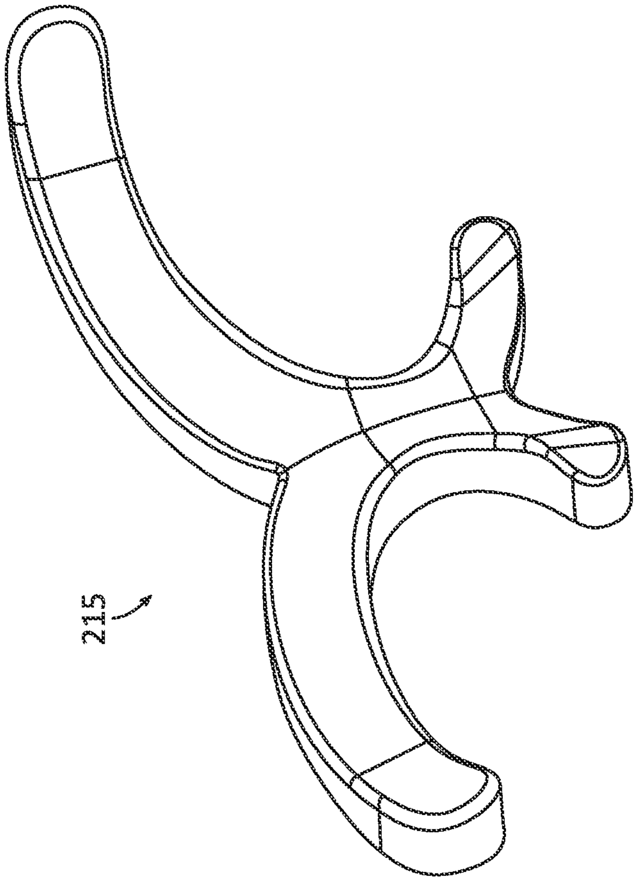
FIG. 4F is another perspective view of the portion of the support assembly of FIG. 4E.
Figure 4E:
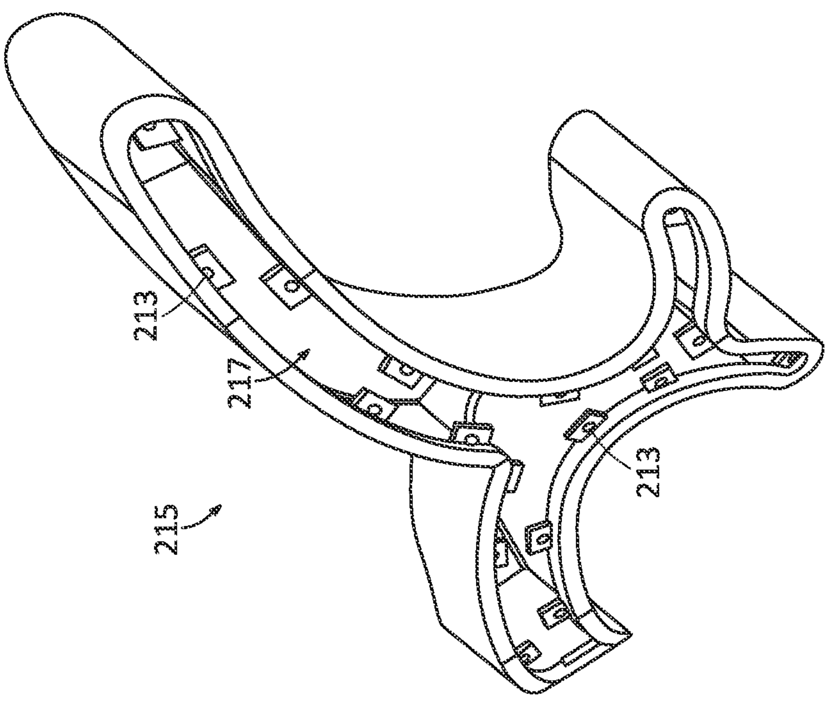
FIG. 4E is a perspective view of a portion of a support assembly of the face mask of FIG. 4A.

FIGS. 4E and 4F show a protective coating 215 of the support assembly 212. The protective coating 215 defines a hollow interior 217 in which compressible material is configured to be disposed.

An outer side of the support assembly 212, e.g., a side of the support assembly 212 configured to face outward away from a user's face with the mask 200 worn on the user's face, is open, as shown in FIG. 4E. In other implementations, the outer side is closed such that the hollow interior 217 is an enclosed space.

In the present disclosure, like-named components of the implementations generally have similar features, and thus within a particular implementation each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described implementations. Accordingly, the present application is not to be limited by what has been particularly shown and described, except as indicated by the appended claims. All publications and references cited herein are expressly incorporated by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

The invention claimed is:

1. A face covering device, comprising:

a base configured to cover at least a portion of a user's face and having formed therein a first eye opening and a second eye opening;

a plurality of light emitting diodes (LEDs) coupled to the base and configured to emit light toward and to skin of the user's face with the base covering at least the portion of the user's face; and a support assembly coupled to the base, the support assembly including a compressible material coated by a protective coating and comprising:

a first eye support comprising a first eyebrow support, a first undereye support located under the first eye opening, and a first portion of a nose support that together define a first eye support opening, wherein a portion of the first eye support is configured to prevent the light emitted toward the user's face from passing through the first eye support opening, and a second eye support comprising a second eyebrow support, a second undereye support located under the second eye opening, and a second portion of the nose support that together define a second eye support opening, wherein a portion of the second eye support is configured to prevent the light emitted toward the user's face from passing through the second eye support opening.

2. The face covering device of claim 1, wherein the support assembly has a shape that follows a shape of eyebrows, an inner side of a left eye, an inner side of a right eye, and a nose.

3. The face covering device of claim 1, wherein the first undereye support is separate and distinct from the first eye support; and the second undereye support is separate and distinct from the second eye support.

4. The face covering device of claim 1, wherein the support assembly is configured to form a seal against the user's face.

5. The face covering device of claim 1, wherein the support assembly is configured to dynamically conform to the user's face.

6. The face covering device of claim 1, wherein the compressible material includes foam, and the protective coating includes silicone.

7. The face covering device of claim 1, wherein the support assembly is configured to facilitate supporting of the base over at least the portion of the user's face.

8. The face covering device of claim 1, further comprising a support configured to be worn on a head of the user with the base covering at least the portion of the user's face.

9. A face covering device, comprising:

a base configured to cover at least a portion of a user's face, wherein the base has a first eye opening and a second eye opening;

a plurality of light emitting diodes LEDs coupled to the base and configured to emit light toward and to skin of the user's face with the base covering at least the portion of the user's face; and a support assembly coupled to the base, the support assembly including a foam coated by silicone and comprising:

a nose support configured to contact at least a portion of the user's nose with the base covering at least the portion of the user's face, a first eyebrow support configured to contact at least one of an orbital bone of the user and a first one of the user's eyebrows with the base covering at least the portion of the user's face, a first undereye support located under the first eye opening and configured to cover a region under a first eye of the user, a second eyebrow support configured to contact at least one of the orbital bone of the user and a second one of the user's eyebrows with the base covering at least the portion of the user's face, and a second undereye support located under the second eye opening and configured to cover a region under a second eye of the user;

wherein a height of one or more of the nose support, the first and second eyebrow supports, and the first and second undereye supports is configured to position the plurality of LEDs at a distance from the user's face with the base covering at least the portion of the user's face.

10. The face covering device of claim 9, wherein the distance is in a range between about 10 mm and about 40 mm.

11. The face covering device of claim 9, wherein the distance of each LED of the plurality of LEDs from the user's face is substantially equal for each LED.

12. The face covering device of claim 9, wherein the distance of at least one LED of the plurality of LED from the user's face is different from the distance of at least one other of the plurality of LEDs from the user's face.

13. The face covering device of claim 9, wherein the height is in a range between about 10 mm and about 40 mm.

14. A face covering device, comprising:

a rigid base having a forehead portion configured to be worn at least partially over a user's forehead, a nose portion configured to be worn at least partially over the user's nose and cheeks, and a chin portion configured to be worn at least partially over the user's chin;

a light assembly coupled to the rigid base and configured to emit light toward and to skin of the user's face; and padding comprising foam coupled to the base, configured to prevent the light emitted toward the user's face from entering the user's eyes, and configured to form a seal against the user's face, the padding further comprising:

a nose support comprising a nose bridge support configured to contact a nose bridge of the user, a first nostril support configured to contact the nose of the user, and a second nostril support configured to contact the nose of the user, a first eyebrow support extending from a first side of the nose support, wherein the first eyebrow support has one or more curves, and a second eyebrow support extending from a second side of the nose support, wherein the second eyebrow support has one or more curves.

15. The face covering device of claim 14, wherein the foam is coated with silicone.

* * * * *